United States Patent [19]

Von Froreich

[11] Patent Number: 4,461,836

[45] Date of Patent: Jul. 24, 1984

[54] APPARATUS FOR THE SETUP AND EVALUATION OF DIFFUSION TESTS IN A GEL MEDIUM

[76] Inventor: André Von Froreich, Föhrengrund 10, 2107 Rosengarten 5, Fed. Rep. of Germany

[21] Appl. No.: 371,680

[22] Filed: Apr. 26, 1982

[30] Foreign Application Priority Data

Apr. 29, 1981 [DE] Fed. Rep. of Germany ....... 3116926

[51] Int. Cl.³ .............................................. C12M 1/28
[52] U.S. Cl. ..................................... 435/294; 435/298
[58] Field of Search ........................ 435/287, 294, 298

[56] References Cited

U.S. PATENT DOCUMENTS 2,533,089 12/1950 Brewer et al. ...................... 435/287
4,246,339 1/1981 Cole et al. ...................... 435/287 X Primary Examiner—Ferris H. Lander
Attorney, Agent, or Firm—Browdy and Neimark

[57] ABSTRACT

An apparatus for applying substance-coated carriers onto a gel layer for microbiological tests makes it possible to position the carriers, in a single hand operation, in a precise spatial relationship with evaluation scales or rings on the gel dish. The substance-coated carriers are secured on projections of a support which, in one position, serves as a closure for the gel dish. When inverted, the support precisely fits into the gel dish by means of corresponding grooves and projections on the support and the gel dish so that the projections press the substance-coated carriers onto precise positions on the gel.

6 Claims, 4 Drawing Figures

APPARATUS FOR THE SETUP AND EVALUATION OF DIFFUSION TESTS IN A GEL MEDIUM

FIELD OF THE INVENTION

The present invention relates to an apparatus for the emplacement of substances-coated carriers and the subsequent reading of the test result, particularly for the microbiological laboratory.

BACKGROUND OF THE INVENTION

For microbiological laboratory test purposes, it is known to use flat dishes of glass or translucent plastic, which are coated with a thin, uniform gel layer. The substance-coated carriers are placed onto this layer and the diffusion of the substance contained in the carriers takes place into this gel layer. Depending upon the test and the substance, the diffiusion results in an inhibition or promotion of the growth of the microorganisms placed upon the gel layer.

The diameter of growth inhibition or growth promotion zones is a measure for the outcome of the test, which in turn makes it possible to reach conclusions as to the utility of a substance as an antibiotic or as to the nature of a microorganism.

As carriers for test substances, round slips of filter paper of small diameter have generally established themselves in practice. The usual methods for applying the individual slips onto the surface of the gel can be classified into three groups:

(A) applying the slips individually with a tweezers and pressing the slips individually against the surface of the gel;

(B) applying a group of slips, which are interconnected spatially with bridges of filter paper, with a tweezers and pressing them individually against the gel surface; and (C) applying a group of carriers with the aid of a mechanical dispensing device which has a plurality of supply containers with slips and causes one slip at a time to drop from each supply container by means of pressure exerted onto a handle and then presses them against the gel surface.

Reading out the test result, which is expressed by a more or less pronounced inhibition or promotion of the growth of the microorganisms in a circle around the point at which they were applied, is at the present time performed in the following ways:

(1) By estimating the diameter of the circular field of growth; this is the most often-used method.

(2) By measurement with a ruler or slide gauge directly or following projection onto a screen.

(3) By comparison with previously prepared, movable scales which are held above the gel or, in the case of a translucent gel, under it.

In cases (A) and (B) above, the application of the slips of paper is associated with numerous manipulations, which impair both the precision with which the slips are placed in position and the rapidity with which this can be accomplished. In case (C), a precondition is an apparatus which involves investment costs and requires a person experienced in its operation. Because it is also necessary to keep relatively large quantities of substance carriers on hand, this manner of applying the slips is suitable only for laboratories with a relatively large volume of work.

Reading out the results by estimation as in category (1) above requires extensive experience and yet is still not reliable.

Using standard measuring rods as in category (2) above, while more precise and producing better results, still is hardly ever used because of the possibility of unintended displacements, parallax errors and time losses. Comparison with previously prepared, movable scales as in (3) is again not entirely reliable because of the danger of unintended displacement and parallax during the reading of the results and is also not free from the necessity for manipulation; in other words, it causes lost time.

SUMMARY OF THE INVENTION

An object of the invention is to make it possible to apply substance-carrying slips and to press them down all with a single hand operation, and to enable the positioning of the slips on the gel in an unmistakably clearly defined position, in order to bring them into a precise spatial relationship with evaluation scales or evaluation rings.

This object is attained in accordance with the present invention in that the substance-carrying slips are secured by the manufacturer of the apparatus on a support in a clearly defined manner and this support can be placed into the dish containing the gel in a precisely and unmistakably defined position by means of protrusions and recesses.

In correspondence with the position of the slips on the support, evaluation scales or markings are disposed on the bottom of the dish, permitting direct visual evaluation of the result of the reaction.

The advantages attainable with the invention are in particular that in addition to the simplicity of manipulating the substance-carrying slips, it is possible to attain an automatic, precise and unmistakable alignment of substance carriers and thus of the reaction fields with respect to evaluation scales or markings.

This apparatus can be produced in such a manner that one-time use is favorable in cost; the smaller laboratory is spared both labor and investment costs; and the apparatus can also be manipulated easily by inexperienced persons. Both the smaller and the larger laboratory gain the opportunity to evaluate the diffusion test with less error and greater accuracy than with conventional methods.

This evaluation can, under precisely standardizable conditions such as exist in the case of the present invention, be used for a quantitative evaluation of tests which otherwise can be evaluated only semiquantitatively and, for instance in the case of resistance tests of microorganisms, can provide the physician who is treating a patient with an additional indication as to the dosage of an antibiotic.

One exemplary embodiment of the inventon is shown in the drawing and described in detail below.

DETAILED DESCRIPTION OF A PREFERRED EMBODIMENT

Figure 1:
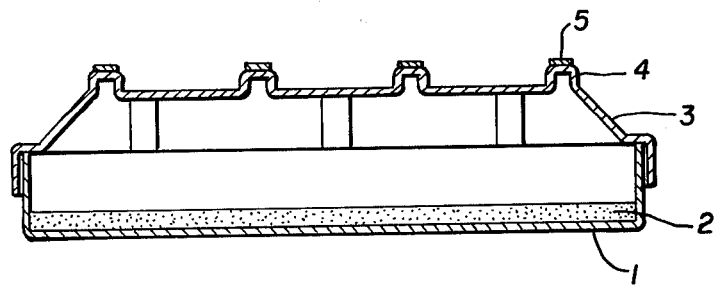
FIG. 1 shows an apparatus in accordance with the present invention, for the setup and evaluation of diffusion tests in a gel medium, seen in section, along line AB in FIG. 3.

As shown in FIG. 1, a gel medium 2 is preplaced in a dish 1. A support 3, on which the substance-coated carriers 5 are secured on imperforate posts or protrusions 4, is fitted in lapped fashion over this dish. The support is embodied in this case as a cap for the dish 1, in order to prevent the gel from drying out or becoming contaminated.

Figure 2:
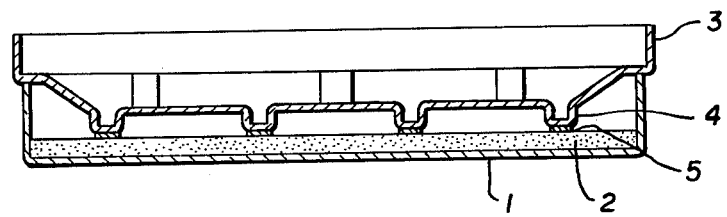
FIG. 2 shows the same apparatus in section, after the support 3 has been turned over.

When it is desired for the substance-coated carriers 5 to contact the gel 2, the support 3 is turned over and fitted into the dish 1, as is shown in FIG. 2. The substance-coated carriers 5 imperforate on the posts or protrusion 4 then rest on the gel 2, and the support 3 closes off the dish from the outside.

Figure 3:
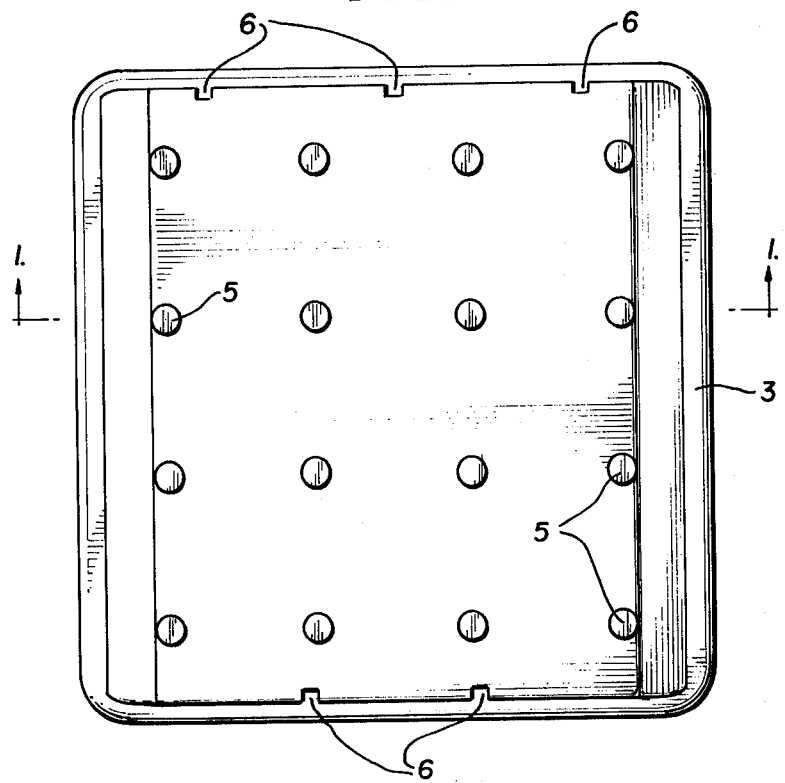
FIG. 3 shows the apparatus in plan view.
Figure 4:
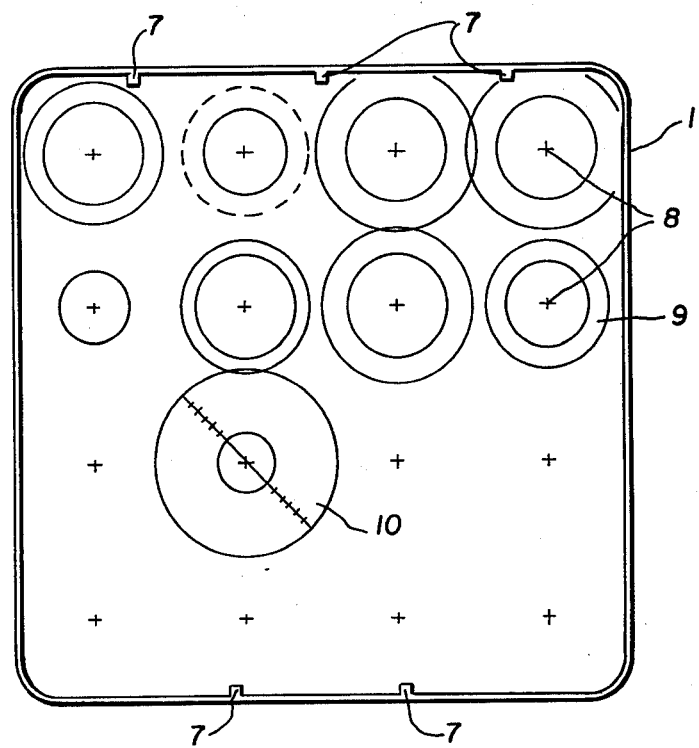
FIG. 4 shows a plan view of the apparatus of the present invention with the cover removed.

From the view shown in FIG. 3, it can be seen that the support 3 is provided with guide recesses 6, into which the protrusions 7 of the guide dish 1 in FIG. 4 fit. The support is thus guided into the desired position, and shifting of the support relative to the dish is made impossible.

In FIG. 4, the positions 8 of the substance-coated carriers are shown, as well as the associated evaluation markings 9 and an evaluation scale 10. The evaluation scale 10, shown only with respect to one carrier position 8 in FIG. 4, is disposed on the bottom of the dish 1 itself, inscribed either on the outside or the inside.

It will be obvious to those skilled in the art that various changes may be made without departing from the scope of the invention and the invention is not to be considered limited to what is shown in the drawings and described in the specification.

What is claimed is:

1. An apparatus for the setup and evaluation of a diffusion test in a get medium, comprising: a dish in which said gel medium is contained, and a support having imperforate protrusions on which substance-coated carriers are secured, said dish and said support including cooperating means for precisely positioning said support, when inverted, atop said dish.

2. An apparatus as defined by claim 1, further comprising one or more scales or markings applied to the bottom of the dish said scales or markings having a fixed spatial relationship with respect to the location at which the substance-coated carriers are applied and permitting the reading out of the reaction results.

3. An apparatus as defined by claim 1, wherein the support for the substance-coated carriers can be used as a closure means for the dish containing the gel both in its right-side-up and its upside-down position.

4. An apparatus as defined by claim 1, said protrusions, on the top of which the carriers can be secured, effect an increase in the distance between the support and the gel medium when said support is inverted.

5. An apparatus for the setup and evaluation of a diffusion test in a gel medium, comprising
   a dish having an upwardly extending side wall and a bottom wall, said dish being adapted to contain a layer of gel medium on said bottom wall to a predetermined depth; and
   a reversable cover member for said dish, said cover member having a first dish-covering position and an inverted second dish-covering position, said cover member presenting, in its first position, imperforate protrusions, at least some of which having secured thereto on the outside surface thereof substance-coated carriers, said dish and said cover member including cooperating means for precisely positioning said cover member on said dish when said support is in its second position, whereby when said cover member is reversed said substance-coated carriers come in contact with the gel medium within said dish.

6. An apparatus according to claim 5, wherein said cover member positioning means comprise guide recesses and said dish positioning means comprise guide protrusions, whereby when said cover member is supported in its second position on said dish, said guide recesses engage said guide protrusions to thereby precisely position said substance-coated carriers at the upper surface of the gel member.

* * * * *